United States Patent
Scibek et al.

(10) Patent No.: US 10,920,185 B2
(45) Date of Patent: Feb. 16, 2021

(54) VESSELS AND SPINNER FLASKS WITH REDUCED IMPELLER WOBBLE FOR CULTURING CELLS

(71) Applicant: Corning Incorporated, Corning, NY (US)

(72) Inventors: Jeffery Joseph Scibek, Horseheads, NY (US); James Clark Walck, Jr., Sayre, PA (US)

(73) Assignee: Corning Incorporated, Corning, NY (US)

(*) Notice: Subject to any disclaimer, the term of this patent is extended or adjusted under 35 U.S.C. 154(b) by 217 days.

(21) Appl. No.: 16/094,233

(22) PCT Filed: May 31, 2017

(86) PCT No.: PCT/US2017/035092
§ 371 (c)(1),
(2) Date: Oct. 17, 2018

(87) PCT Pub. No.: WO2017/210236
PCT Pub. Date: Dec. 7, 2017

(65) Prior Publication Data
US 2019/0112567 A1    Apr. 18, 2019

Related U.S. Application Data

(60) Provisional application No. 62/343,321, filed on May 31, 2016.

(51) Int. Cl.
*C12M 3/00*    (2006.01)
*C12M 1/00*    (2006.01)
(Continued)

(52) U.S. Cl.
CPC ......... *C12M 27/02* (2013.01); *B01F 13/0827* (2013.01); *C12M 23/08* (2013.01);
(Continued)

(58) Field of Classification Search
CPC ....... C12M 27/18; C12M 27/02; C12M 27/20
See application file for complete search history.

(56) References Cited

U.S. PATENT DOCUMENTS 2,958,517 A * 11/1960 De Long ................ C12M 27/02
                                                            435/302.1
3,603,563 A *  9/1971 Holland ................. B01F 7/163
                                                            366/317
(Continued)

FOREIGN PATENT DOCUMENTS

CN    201981197 U    9/2011
CN    102409020 A    4/2012
(Continued)

OTHER PUBLICATIONS

International Search Report and Written Opinion of the International Searching Authority; PCT/US2017/035092; dated Aug. 8, 2017; 11 Pages; European Patent Office.
(Continued)

*Primary Examiner* — Nathan A Bowers
(74) *Attorney, Agent, or Firm* — F. Brock Riggs

(57) ABSTRACT

A vessel for culturing cells is provided that includes a vessel body having a top portion, a bottom portion comprising a bottom interior surface, and a cylindrical sidewall. The vessel additionally has an impeller assembly inside the vessel body having a top portion rotatably coupled to the top portion of the vessel body, the impeller assembly having a plurality of planar blades, a central axis, a flexible shaft extending down from the top portion of the impeller assembly, a magnet receptacle molded within the plurality of planar blades, a magnet within the magnet receptacle, and an impeller o-ring coupled to a bottom surface of the planar blades. The vessel also includes a plurality of positioning
(Continued)

nubs coupled to the bottom interior surface of the vessel body, spaced from an inside edge of the impeller o-ring.

20 Claims, 14 Drawing Sheets

(51) Int. Cl.
    *C12M 1/06*     (2006.01)
    *C12M 1/24*     (2006.01)
    *B01F 13/08*     (2006.01)
    *B01F 7/00*     (2006.01)

(52) U.S. Cl.
    CPC ............ *C12M 23/28* (2013.01); *C12M 23/38* (2013.01); *C12M 27/20* (2013.01); *B01F 7/0025* (2013.01)

(56) References Cited

U.S. PATENT DOCUMENTS

| | | | |
|---|---|---|---|
| 3,649,465 A | | 3/1972 | Scharf et al. |
| 3,856,138 A | * | 12/1974 | Maekawa ........... B65D 81/3222 |
| | | | 206/221 |
| 4,289,854 A | | 9/1981 | Tolbert et al. |
| 4,946,286 A | * | 8/1990 | Purkapile ............ B01F 11/0054 |
| | | | 366/243 |
| 5,407,270 A | * | 4/1995 | Barile ..................... A47J 43/27 |
| | | | 366/247 |
| 6,109,780 A | | 8/2000 | Lesniak |
| 6,593,128 B1 | | 7/2003 | Kiy et al. |
| 7,790,456 B2 | | 9/2010 | Terstegge et al. |
| 7,985,387 B2 | | 7/2011 | Haywood et al. |
| 8,057,092 B2 | | 11/2011 | Ryan et al. |
| 8,822,209 B2 | | 9/2014 | Oldenburg et al. |
| 8,982,156 B2 | | 3/2015 | Maggiore |
| 9,700,857 B1 | * | 7/2017 | Larsen ................ B01F 7/00691 |
| 2003/0008389 A1 | * | 1/2003 | Carll ....................... B01F 11/04 |
| | | | 435/302.1 |
| 2008/0131957 A1 | | 6/2008 | Ryan et al. |
| 2008/0166328 A1 | | 7/2008 | Harmon et al. |
| 2008/0194010 A1 | | 8/2008 | Liu |
| 2011/0003366 A1 | * | 1/2011 | Zeikus ................... C12M 27/00 |
| | | | 435/243 |
| 2012/0208266 A1 | | 8/2012 | Bookbinder et al. |
| 2015/0252315 A1 | * | 9/2015 | Wada ................ B01F 15/00175 |
| | | | 435/377 |
| 2016/0001931 A1 | | 1/2016 | Seippel |
| 2017/0081638 A1 | | 3/2017 | Ma |

FOREIGN PATENT DOCUMENTS

| | | |
|---|---|---|
| CN | 204434618 U | 7/2015 |
| JP | 8140692 A | 6/1996 |
| KR | 199107609 B1 | 9/1991 |
| WO | 2009009771 A1 | 1/2009 |

OTHER PUBLICATIONS

Rao et al; "Disposable Bioprocessing: The Future Has Arrived"; Biotechnology and Bioengineering, vol. 102, No. 2, (2009); p. 348-356.

* cited by examiner

VESSELS AND SPINNER FLASKS WITH REDUCED IMPELLER WOBBLE FOR CULTURING CELLS

CROSS-REFERENCE TO RELATED APPLICATIONS

This is a national stage application under 35 U.S.C. § 371 of International Application No. PCT/US2017/035092, filed on May 31, 2017, which claims the benefit of priority of U.S. Provisional Application Ser. No. 62/343,321 filed on May 31, 2016, the content of which is relied upon and incorporated herein by reference in its entirety.

TECHNICAL FIELD

The present disclosure relates generally to spinner flasks and vessels for culturing cells. More particularly, embodiments described herein relate to disposable spinner flask vessels having an impeller assembly.

BACKGROUND

In various scientific fields, it is useful to grow cells in a culture media (such as a liquid suspension) over an extended period of time. However, increasing cell numbers result in the depletion of nutrients in the culture medium. When the media is allowed to stagnate, cell growth is inhibited due to the local depletion of nutrients and the cells can die.

In general, it is understood that a cell culture suspension must be stirred in order to effectively grow cells. Optionally, microcarriers to which cells may be attached may be suspended in cell culture media. A spinner flask is a type of cell culture vessel that employs a suspended impeller driven by an external rotating magnet under the base of the spinner flask to maintain the cells in suspension. The design of the suspended impeller is complicated since many different factors must be balanced to properly influence the suspension of cell cultures such as the hydrodynamic stress imparted on growing cells that can damage them or alter their morphology. In addition, the blade design and movement must keep the cells suspended but not shear the cells or the microcarriers.

Further, care must be taken not to contaminate the culture media. Spinner flasks have typically consisted of glass and metal reusable cell culture vessels comprising an amalgam of working parts each of which requires cleaning, sterilization (usually by autoclave) and proper storage between uses. When such an amalgam of working parts is used for a spinner flask, the user can spend considerable time keeping track of the parts and maintaining the proper conditions for culturing cells.

There accordingly remains a need for an inexpensive, disposable, pre-sterilized, fully integrated cell culture vessel which provides gentle stirring to keep cells suspended and prevent shearing.

SUMMARY

Described herein are various embodiments of a disposable spinner flask vessel for culturing cells having an impeller assembly stabilized by a plurality of positioning nubs.

According to an aspect of the present disclosure, a vessel for culturing cells is provided that includes a vessel body having a top portion, a bottom portion having a bottom interior surface, and a cylindrical sidewall. The vessel additionally has an impeller assembly inside the vessel body having a top portion rotatably coupled to the top portion of the vessel body, the impeller assembly having a plurality of planar blades, a central axis, a flexible shaft extending down from the top portion of the impeller assembly, a magnet receptacle molded within the plurality of planar blades, a magnet within the magnet receptacle, and an impeller o-ring coupled to a bottom surface of the planar blades. The vessel also includes a plurality of positioning nubs coupled to the bottom interior surface of the vessel body, spaced from an inside edge of the impeller o-ring.

According to another aspect of the present disclosure, a vessel for culturing cells is provided that includes a vessel body having a top portion, a bottom portion having a bottom interior surface, and a cylindrical sidewall. The vessel also includes an impeller assembly inside the vessel body having a top portion rotatably coupled to the top portion of the vessel body, the impeller assembly having a plurality of planar blades, a central axis, a flexible shaft extending down from the top portion of the impeller assembly, a magnet receptacle molded within the plurality of planar blades, a magnet within the magnet receptacle, and an impeller o-ring coupled to a bottom surface of the planar blades. The vessel further includes a plurality of positioning nubs coupled to the bottom interior surface of the vessel body, spaced from an inside edge of the impeller o-ring; and a center nub coupled to the bottom interior surface of the vessel body coincident with the central axis of the impeller assembly.

Additional features and advantages will be set forth in the detailed description which follows, and in part will be readily apparent to those skilled in the art from that description or recognized by practicing the embodiments as described herein, including the detailed description which follows, the claims, as well as the appended drawings.

It is to be understood that both the foregoing general description and the following detailed description are merely exemplary, and are intended to provide an overview or framework to understanding the nature and character of the claims. The accompanying drawings are included to provide a further understanding, and are incorporated in and constitute a part of this specification. The drawings illustrate one or more embodiments, and together with the description serve to explain principles and operation of the various embodiments.

DETAILED DESCRIPTION

As used herein, the term "and/or," when used in a list of two or more items, means that any one of the listed items can be employed by itself, or any combination of two or more of the listed items, can be employed. For example, if a composition is described as containing components A, B, and/or C, the composition can contain A alone; B alone; C alone; A and B in combination; A and C in combination; B and C in combination; or A, B, and C in combination.

In this document, relational terms, such as first and second, top and bottom, and the like, are used solely to distinguish one entity or action from another entity or action, without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

Several currently available large-volume spinner flasks have been demonstrated to be incompatible with microcarrier cultures. Use of these flasks result in physical damage to both microcarriers and attached cells. A root cause for this damage to cells, cells attached to the microcarriers, and/or the microcarrier's themselves is believed to be due to impeller contact between a central nub and other features of the vessel. Insufficient clearance between a bottom surface of the impeller blade and the top of a raised feature on the bottom of the vessel can also cause cell damage.

Figure 1:
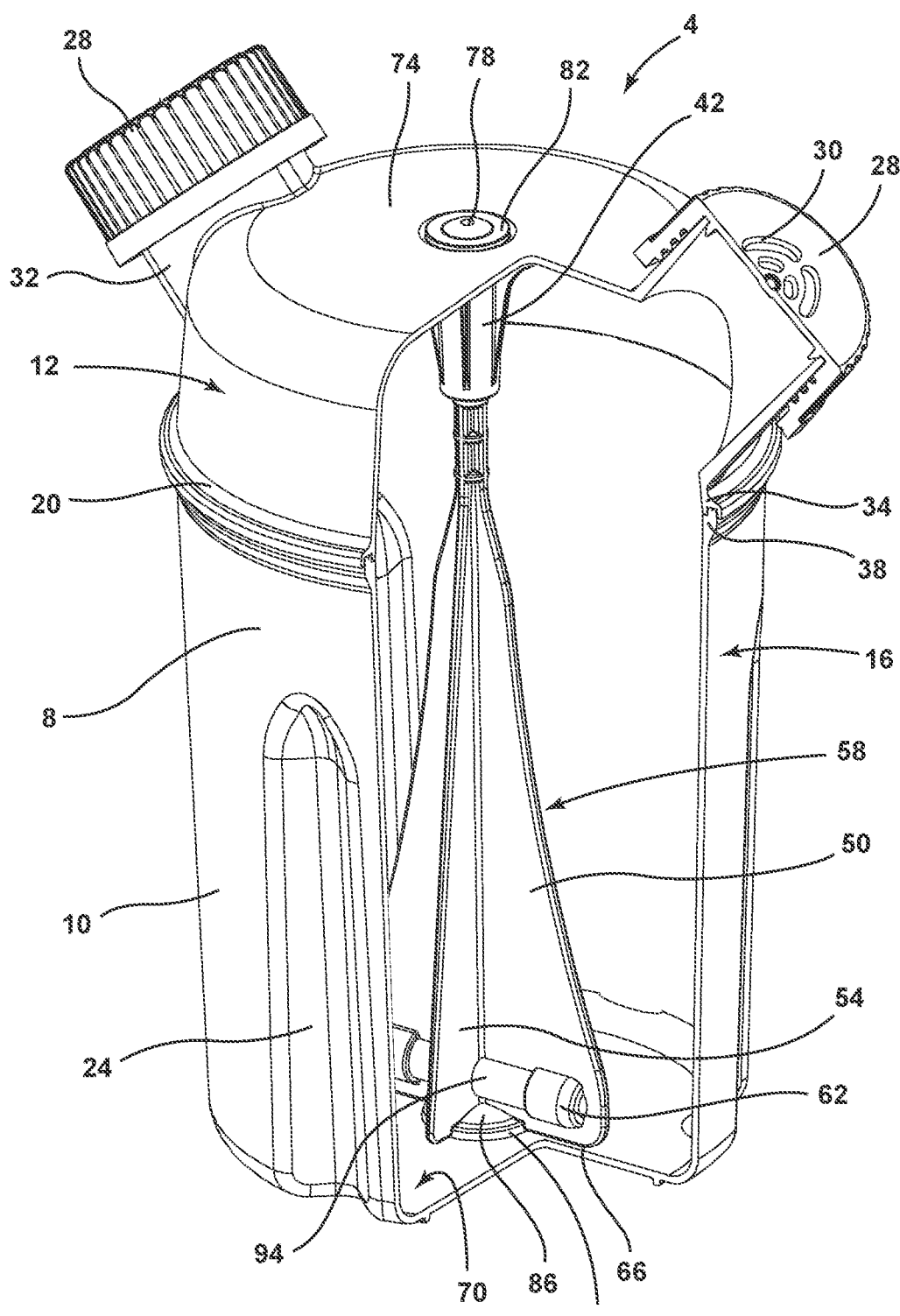
FIG. 1 is a cut-away perspective view of an embodiment of a spinner flask.
Figure 2:
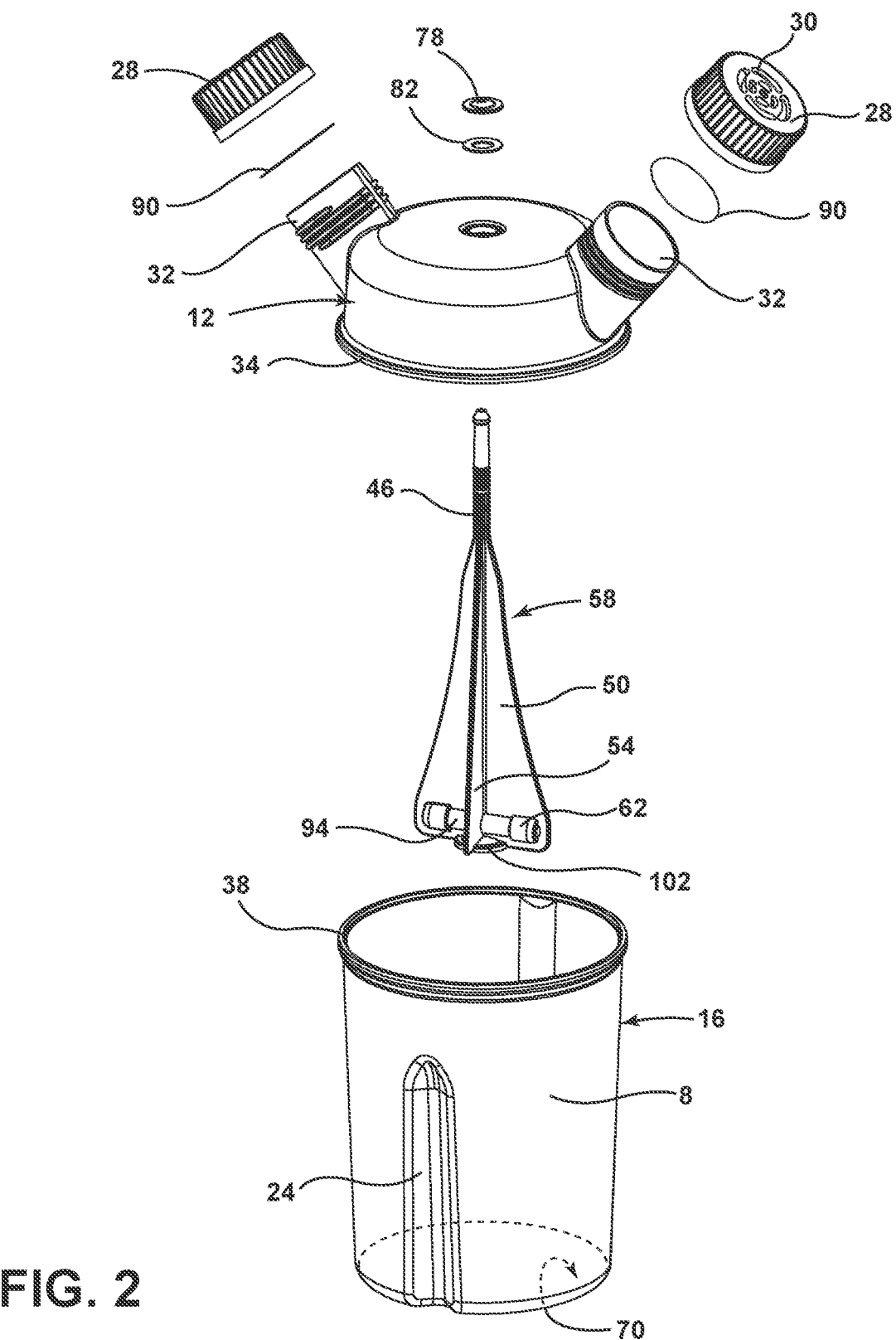
FIG. 2 is an exploded view of the flask depicted in FIG. 1.
Figure 3:
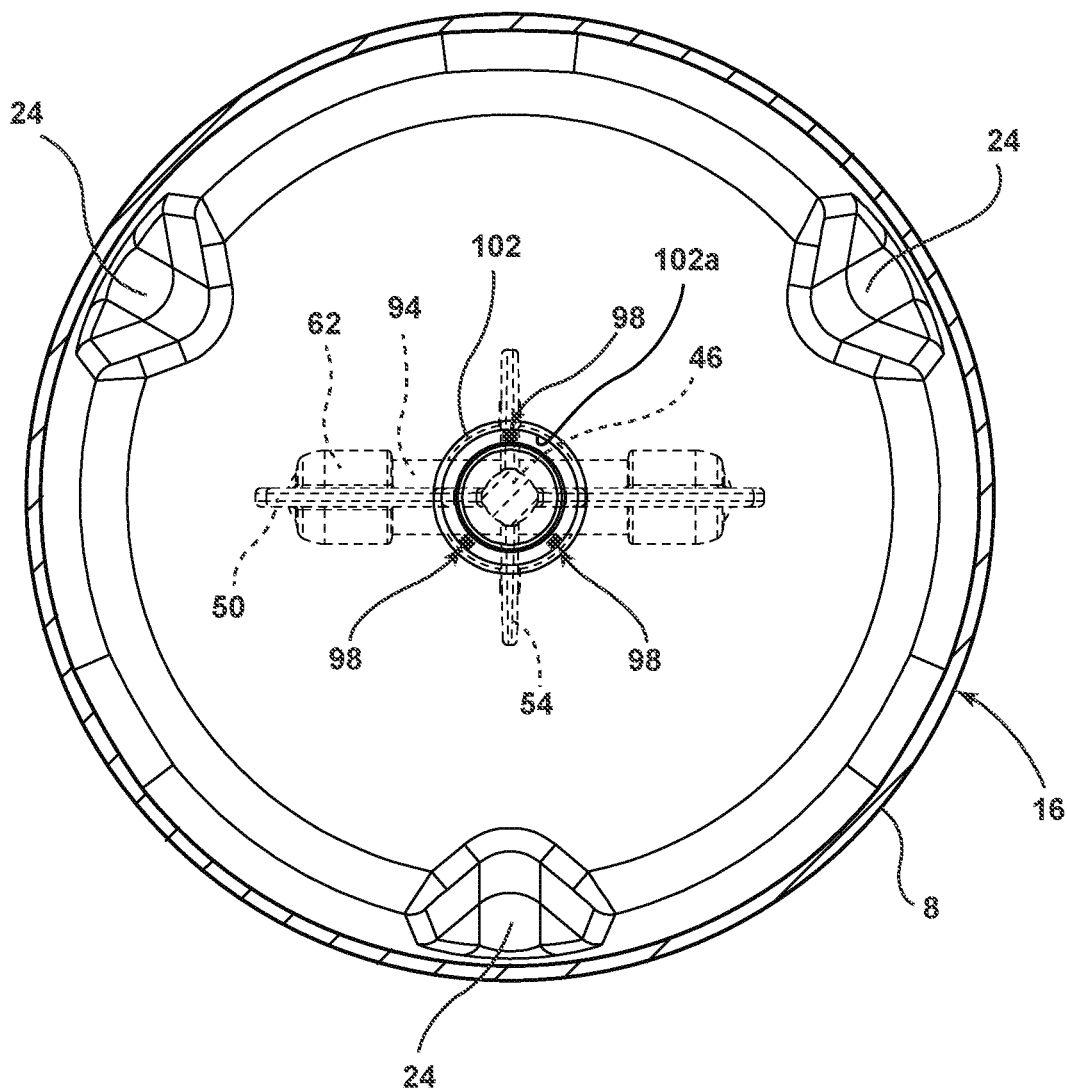
FIG. 3 is a cut-away top view of a spinner flask showing a lower impeller assembly and a plurality of positioning nubs according to an embodiment.
Figure 4:
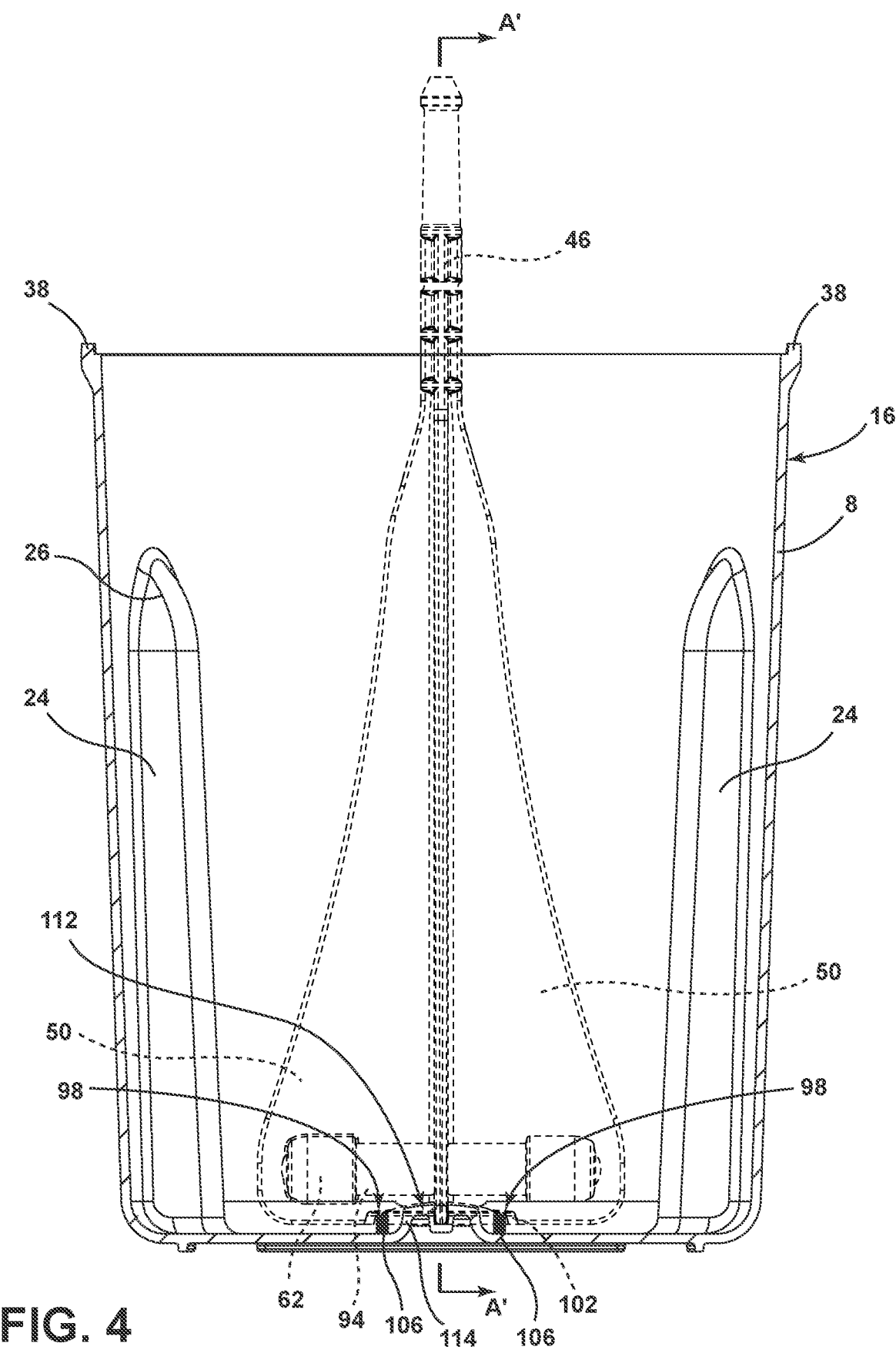
FIG. 4 is a cut-away side view of a lower impeller assembly and a plurality of cylindrical positioning nubs according to an embodiment.
Figure 5:
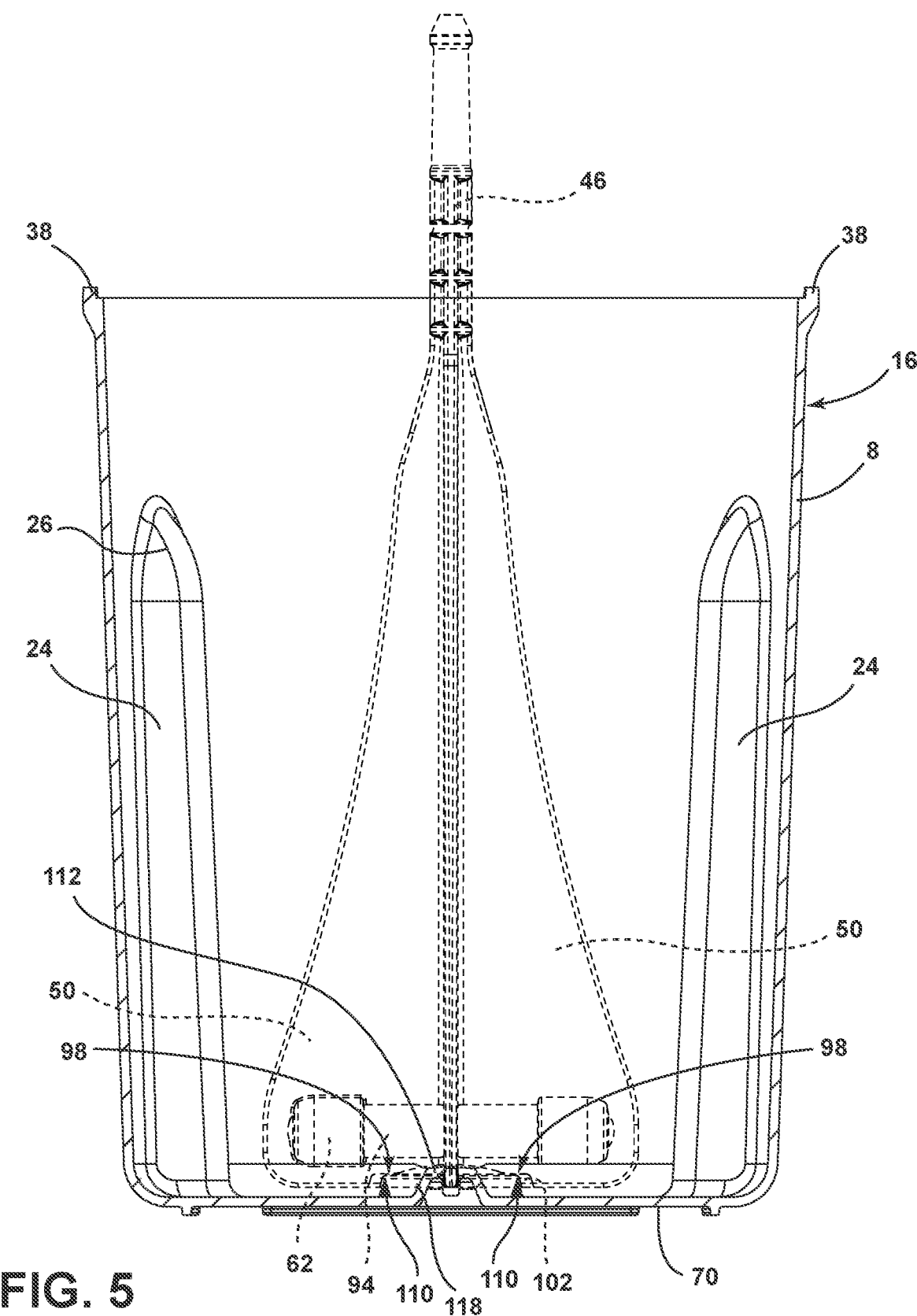
FIG. 5 is a cut-away side view of the bottom of an impeller assembly and a plurality of conical positioning nubs according to an embodiment.

Referring to FIGS. 1-11, a vessel 4 for culturing cells is shown in exemplary form according to aspects of the disclosure. The vessel 4 comprises a vessel body 8 having a top portion 12 and a bottom portion 16, one or more necked access ports 32, and an impeller assembly 58. The top portion 12 and the bottom portion 16 are circumferentially sealed along a weld line 20 which is the result of a joining of a top interconnecting lip 34 and a bottom interconnecting lip 38 circumscribing the periphery of both portions. The vessel 4 has a substantially cylindrical shape and a central axis A-A' with an inner surface, an outer surface, a top part 74, a sidewall 10, and a bottom interior surface 70 having a center nub 112. In certain aspects the center nub 112 can be a cylindrical center nub 114 (FIG. 4) or a conical center nub 118 (FIG. 5). Although any size vessel is theoretically possible, the sizes for stirring vessels of aspects of the disclosure typically range from 125 ml to 10 liters and specific sizes include a one liter, two liter, and a three liter version.

The impeller assembly 58 includes a center shaft 46 extending along a A-A' central axis. In different aspects of the present disclosure, the center shaft 46 may be flexible, rigid, or possess other varying amounts of flexibility. Extending from and contiguous with the shaft 46 are four planar blades 50, 54 each disposed 90 degrees relative to each other. Of the four planar blades 50, 54 there are two major blades 50 and two minor blades 54. The major blades 50 are disposed 180 degrees relative to one another and likewise, the two minor blades 54 are disposed 180 degrees relative to each another. The arrangement of blades 50, 54 around the central shaft 46 creates an alternating effect of a minor-major blade orientation. It is believed that this orientation provides enhanced mixing of fluid in both the lateral as well as vertical planes within the vessel 4. The blades 50, 54 represent planes that are oriented vertically when the vessel 4 is sitting upright. As understood by those with ordinary skill in the art, other blade configurations, shapes, and arrangements can be employed in this disclosure, including those that employ fewer or more than four blades.

With reference to FIGS. 3-6, at the bottom of the shaft 46 and beneath the major and minor blades 50, 54 of the impeller assembly is an impeller o-ring 102. The impeller o-ring 102 is coupled to a bottom cut-out portion 86 of the planar blades and the bottom edge of the impeller o-ring may be even with a bottom edge 66 of the planar blades 50, 54. A plurality of positioning nubs 98 are coupled to the bottom interior surface 70 spaced from or along an inside edge 102a of the impeller o-ring 102. In some embodiments, the group of positioning nubs can have two, three, four, five, six, or more positioning nubs 98 spaced apart from each other along the inside edge 102a of the impeller o-ring 102. In embodiments, the plurality of positioning nubs 98 may be spaced an equal distance from one another along the inside edge 102a of the impeller o-ring 102. In an embodiment, the plurality of positioning nubs is three positioning nubs 98, each nub spaced an equal distance from one another. The plurality of positioning nubs can have each nub spaced an equal distance from one another along the inside edge 102a of the impeller o-ring 102.

Figure 6:
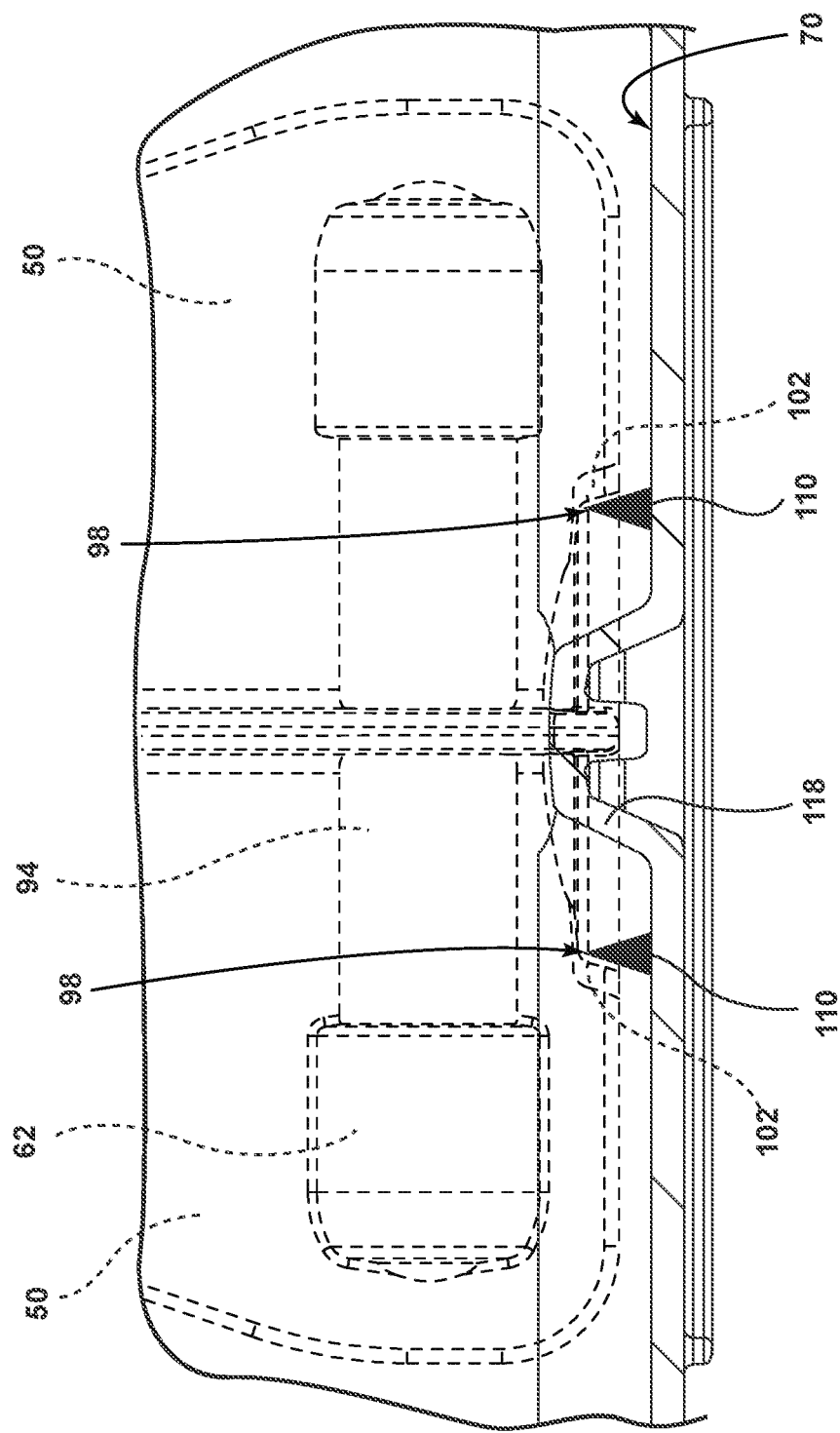
FIG. 6 is an enlarged cut-away side view of the impeller assembly and positioning nubs depicted in FIG. 5 according to an embodiment.
Figure 7:
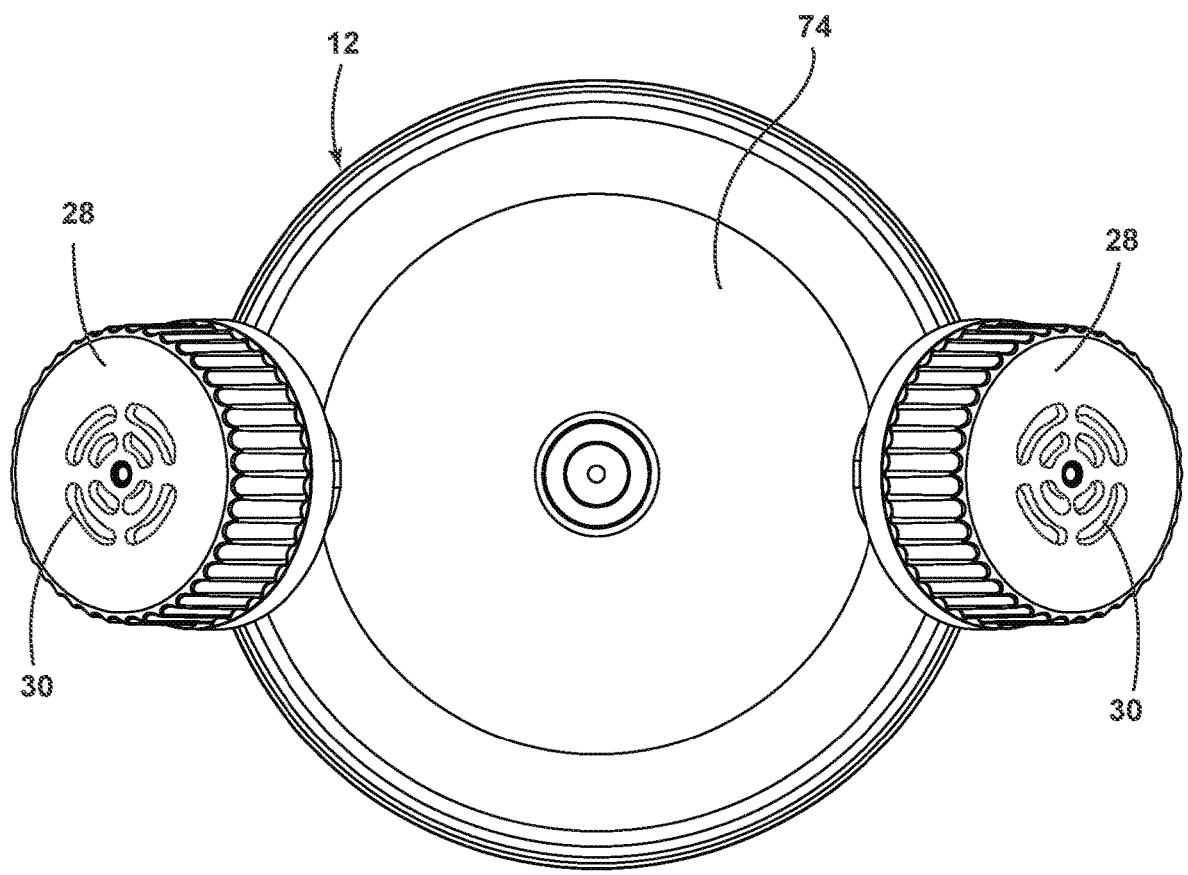
FIG. 7 is a top perspective view of an embodiment of a spinner flask.

The plurality of positioning nubs 98 may comprise individual nubs that have a cylindrical, block, square, conical, rectangular, or pyramidal shape. The plurality of positioning nubs 98 can also have other shapes or combinations of shapes. In FIG. 4, for example, the plurality of positioning nubs 98 is shown as cylindrical positioning nubs 106. In FIGS. 5-6, the plurality of positioning nubs 98 is shown as conical positioning nubs 110. In certain aspects, the shape of the positioning nubs 98 can be configured to make constant, periodic, or frequent contact with the inside edge 102a of the impeller o-ring 102 to prevent perpendicular or lateral movement of the impeller assembly 58. The plurality of positioning nubs 98 minimize impeller wobble thus reducing contact between the impeller assembly 58 and the center nub 112 positioned at the bottom interior surface 70 of the vessel 4.

The center nub 112 is a raised feature as shown in FIGS. 4-6 and can comprise various shapes. For example, the center nub 112 can be configured as a cylindrical center nub 114, as shown in FIGS. 4 and 6. In another embodiment, the center nub 112 can be configured as a conical center nub 118, as shown in FIG. 5. The center nub 112 may include cylindrical, block, square, conical, rectangular, pyramidal, or any other shaped nub. In some embodiments, the center nub 112 can have rounded or beveled edges. The center nub 112 serves at least two purposes: 1) to prevent microcarriers and/or cells from pooling or grouping together below the impeller assembly 58; and 2) to minimize the perpendicular or lateral movement of the impeller assembly 58 during shipment and spinning to avoid impeller breakage. Although the raised center nub 112 can help minimize the perpendicular or lateral movement of the impeller assembly 58, the positioning nubs 98 may also help minimize the perpendicular or lateral movement of the impeller assembly 58.

In some embodiments, the distance between the top surface of the center nub 112 and the bottom of the impeller assembly 58 can be from about 0.001 inches to about 0.1 inches. In other embodiments, the distance between the top of the center nub 112 and the bottom of the impeller assembly 58 can be from about 0.005 inches to about 0.05 inches. In still other embodiments, the distance between the top of the center nub 112 and the bottom of the impeller assembly 58 can be from about 0.01 inches to about 0.03 inches. For example, the distance between the top of the center nub 112 and the bottom of the impeller assembly 58 can be about 0.0150 inches, about 0.0185 inches, about 0.0200 inches, about 0.0250 inches, or all distance values between these recited values and ranges disclosed herein. The tolerance for the plurality of positioning nubs 98, the center nub 112, the impeller assembly 58, and other dimensional features of vessel 4 is about +/−0.005 inches. In some embodiments, the tolerance for the plurality of positioning nubs 98, the center nub 112, the impeller assembly 58, and other dimensional features of vessel 4 is from +/−0.001 inches to +/−0.100 inches.

In some embodiments, the distance between the base outer diameter (diameter of the center nub where connected to bottom interior surface) of the center nub 112 and the inner diameter of the impeller o-ring 102 can be from about 0.01 inches to about 1.0 inches. In other embodiments, the distance between the base outer diameter of the center nub 112 and the inner diameter of the impeller o-ring 102 can be from about 0.1 inches to about 0.5 inches. In still other embodiments, the distance between the base outer diameter of the center nub 112 and the inner diameter of the impeller o-ring 102 can be from about 0.2 inches to about 0.3 inches. For example, the distance between the base outer diameter of the center nub 112 and the inner diameter of the impeller o-ring 102 can be about 0.15 inches, about 0.20 inches, about 0.025 inches, about 0.030 inches, about 0.035 inches, or all distance values between these recited values and ranges disclosed herein.

The spinner flasks and vessels for culturing cells disclosed herein have the ability to offer a readily available, affordable, disposable, pre-sterilized, fully integrated cell culture vessel 4 which provides gentle stirring to minimize hydrodynamic shearing and keep cells suspended in the vessel 4. A center nub 112 and/or positioning nubs 98 on the bottom interior surface 70 of the flask can prevent pooling of microcarriers and/or cells below the impeller assembly 58 and also can minimize the perpendicular movement of the impeller assembly 58 during shipping and spinning to prevent damage to the microcarriers, cells, and/or impeller assembly 58.

Figure 10:
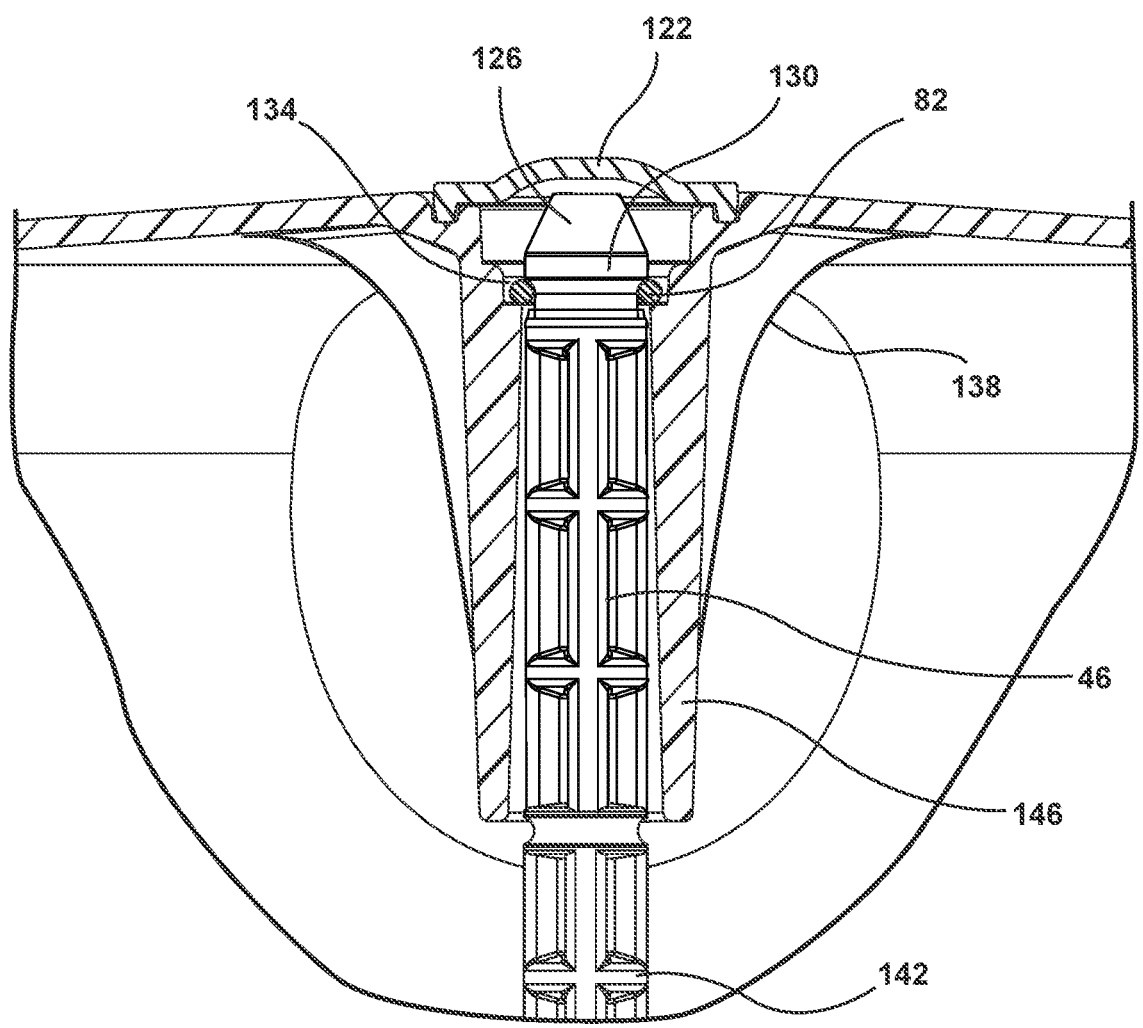
FIG. 10 is an enlarged view of the upper impeller assembly and shaft.
Figure 11:
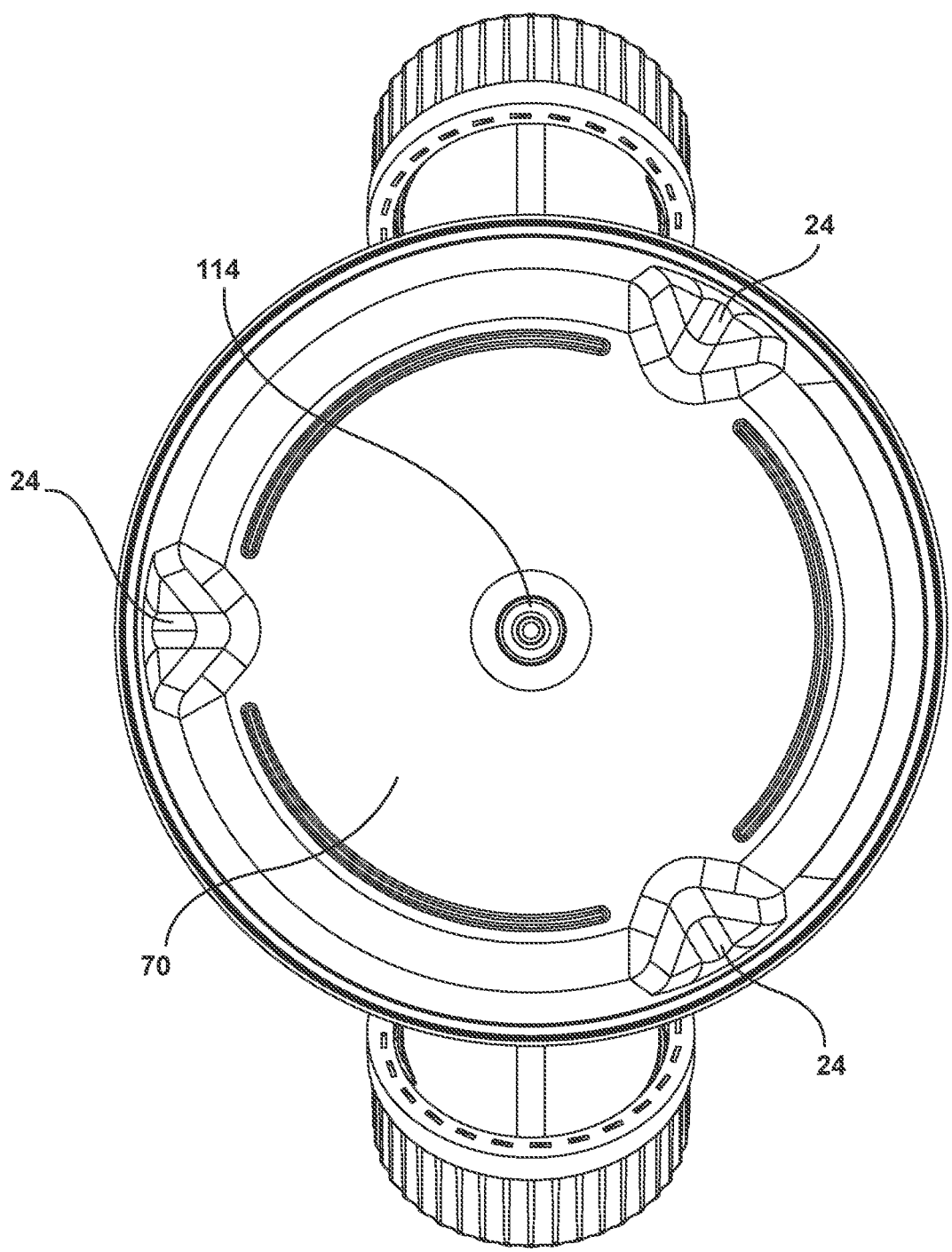
FIG. 11 is a bottom perspective view of an embodiment of a spinner flask.

With reference to FIG. 10, the center shaft 46 has a substantially tapered top end 126 that is mounted in the top portion 12 of the vessel 4 by contact with a shaft receptacle 138 centrally located and integral with the top part 74 of the top portion 12 of the vessel 4. An o-ring 82 is located upon a receiving groove 130 on the shaft 46. The o-ring 82 may be made from PTFE, nylon or other similar low-friction material. The o-ring 82 rests against a circular shelf 134 in such a way that the impeller assembly 58 hangs freely within the vessel 4. By having this single mounting point in the shaft receptacle 138, the flexible shaft 46 is free to rotate. A disc top 122 in the top part 74 seals the shaft receptacle 138 from the external environment. The center shaft 46 further advantageously has a plurality of horizontal support ribs 142 that enhance the stiffness of the shaft 46. The shaft receptacle 138 has sidewalls that extend into the vessel 4 creating a sleeve 146 for receiving the shaft. The sleeve 146 maintains the shaft's 46 orientation within the central axis A-A' and prevents any lateral movement of the impeller assembly 58 within the vessel 4.

The bottom cut-out portion 86 of the impeller assembly 58 is shaped within the intersection of the bottom edges 66 of the respective blades 50, 54. The bottom cut-out portion 86 substantially follows the contour of the cylindrical center nub 114 or conical center nub 118. The impeller o-ring 102 coupled to the bottom cut-out portion 86 of the impeller assembly 58 is not intended to contact the cylindrical and conical center nubs 114, 118 when the vessel 4 is positioned in an upright position. In fact, there may be no contact points between the impeller assembly 58 and the vessel 4 below the shaft receptacle 138. This is advantageous in that it helps reduce the possibility of cell damage if cells, microcarriers, or cells cultured on microcarriers are caught between the bottom edges 66 of the blades 50, 54 and the center nubs 114, 118, or due to shear. The cylindrical and conical center nubs 114, 118 on the bottom interior surface 70 also eliminate any potential dead spots (spots where turbulence created by the spinning impeller is at a minimum) directly below the central axis A-A' of the impeller assembly 58. The bottom cut-out portion 86 within the intersection point of the blades 50, 54 allows the blade edges 66 to come into close proximity with the bottom interior surface 70. In an embodiment, the distance between the blades 50, 54 and the bottom interior surface 70 is between about 0.05 inches and about 0.5 inches. Since the vessel 4 is intended to be shipped as an integral unit, the impeller o-ring 102 in combination with the center nub 112 also serve to contain the impeller 58 during shipping in such a way that the impeller assembly 58 cannot disengage from the bottom of the vessel 4 or damage the sidewall 10 through contact caused by jostling of the vessel 4.

Figure 8:
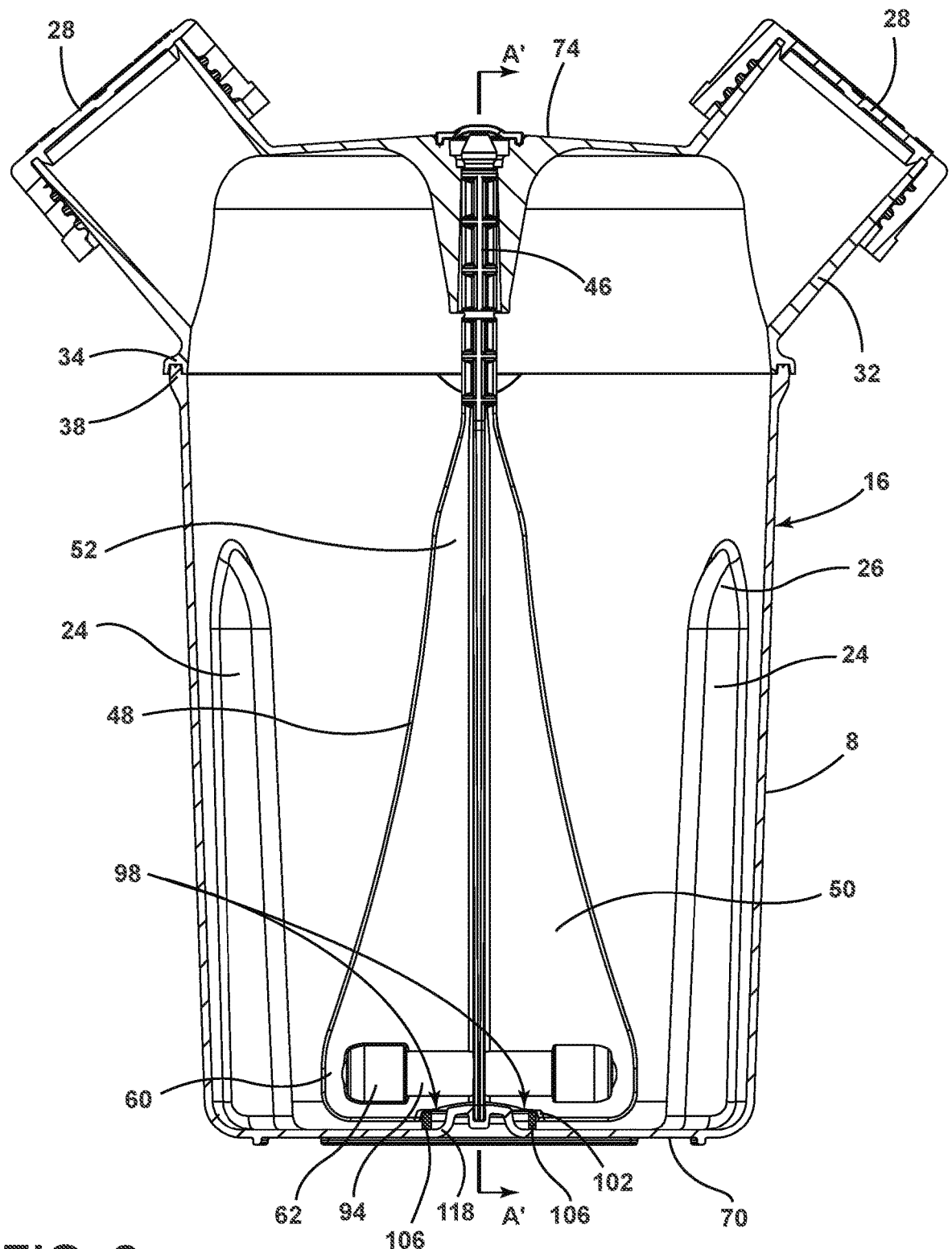
FIG. 8 is a cross section view taken along the A-A' axis of FIG. 4.
Figure 9:
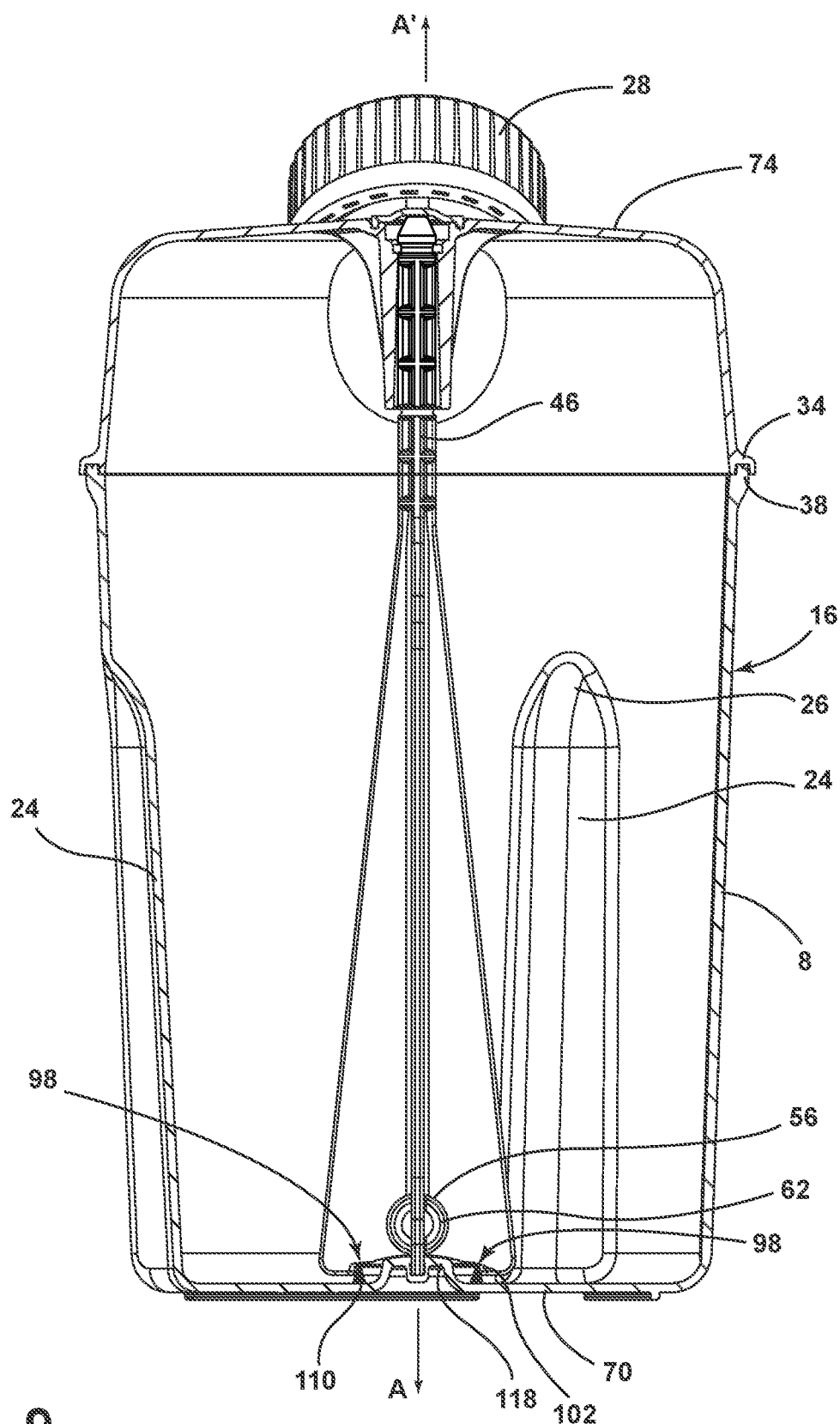
FIG. 9 is a cross section view taken along the A-A' axis of FIG. 4 rotated 90°.

Referring specifically to FIG. 8, which is a vertical cross section of the vessel 4 of an embodiment, each major blade 50 includes an upper portion 52 and a lower portion 60. The upper portion 52 has a substantially triangular shape with an outer edge progressively angled away from the shaft 46 and central axis A-A'. The lower portion 60 of each major blade 50 is substantially rectangular in shape. Referring specifically to FIG. 9, which is a cross section of the vessel 4 taken 90 degrees from the section represented by FIG. 8, the minor blades 54 form a triangular shape along their entire length. An outer edge 48 of each minor blade 54 extends linearly away from the central axis A-A' to a point at the bottom edge 66 of the blades 50, 54. The bottom edges 66 of the lower portion of all blades 50, 54 (minor and major) extend generally parallel to the bottom interior surface 70 of the vessel, but do not contact the bottom interior surface 70. The impeller assembly 58 including blades 50, 54 may be made from polypropylene, TPE, a silicone, or other appropriate polymeric materials.

A magnet receptacle 62 for receiving a magnetic stir bar (magnet) 94 is molded into each lower portion 60 of the two major blades 50. A hole 56 in the minor blades 54 and shaft 46 area completes the magnet receptacle 62. A cylindrical plug or magnetic stir bar 94 is mounted in the magnet receptacle 62 along the lower edge of the two major blades 50 and orthogonal to the minor blades 54. Alternatively, the magnet 94 itself is molded into the impeller assembly 58. To accomplish this, the magnet 94 is inserted into a mold and the impeller assembly 58 is over-molded around the magnet 94 itself. Having the magnet 94 integrally molded within the impeller assembly 58 provides the advantage that during assembly and shipping, the magnet 94 cannot detach from the impeller assembly 58 and damage the vessel body 8.

The one or more access ports 32 extend outward from the top portion 12 of the vessel 4. Optional internally threaded sealing caps 28 are installed on exteriorly threaded access ports 32. In an embodiment, the sealing cap 28 has within it a hydrophobic membrane insert 90 made from material that will allow gas transport into the vessel interior but prevent liquid from escaping the vessel 4 and other contaminants from entering the vessel 4. Examples of such membrane material include polytetrafluoethylene and polyvinylidene-fluoride (PVDF). In some embodiments, the sealing caps 28 further have a vent 30 that allows the necessary gaseous communication with the external environment. In another embodiment, accessories such as tubes may be employed and connected to the one or more access ports 32 to allow aseptic dispensing.

In an embodiment, the one or more access ports 32 extend at an angle from horizontal to allow instruments such as pipettes to pass by impeller assembly 58 and reach adjacent regions of stirring vessels having preselected depths. Nevertheless, the dimensions of the one or more access ports 32 and the angles in which the access ports 32 extend from the vessel body 8 may be selected to optimize instrument accessibility to regions within various vessels 4. Further, in some embodiments, the one or more access ports is two access ports 32 as disclosed in the FIGS., but it will be appreciated that any number of ports 32 are possible.

A plurality of baffles 24 extend along the interior wall in a vertical direction which is parallel to the central axis A-A'. Each baffle 24 has roughly the cross sectional shape of a half-cylinder or an isosceles triangle. Each baffle 24 originates from the vessel bottom 70 and extends vertically upward terminating in an elliptical shape 26. While the baffles 24 illustrated herein are shown to terminate in an elliptical shape 26, embodiments of the present disclosure are not so limited, and any shape may be employed. It is believed that having the plurality of baffles 24 extend completely through the liquid region (i.e. from the bottom interior surface 70 to a point above the liquid surface) enhances turbulence throughout the entire liquid domain. The plurality of baffles 24 project into the vessel cavity, in combination with the impeller assembly 58, create and enable turbulence with the vessel interior. The plurality of baffles 24 are preferably formed integrally with the wall of the container. In some embodiments, the plurality of baffles 24 is three baffles 24, each baffle is spaced an equal distance from each of the other baffles around a perimeter defined by the cylindrical sidewall. In other aspects, the plurality of baffles is disposed symmetrically along the interior cylindrical sidewall, but the number and density of baffles 24 may vary based on vessel size. In embodiments, each baffle is integral with the sidewall of the vessel body originating at the bottom interior surface and extending vertically to a predetermined distance up the sidewall.

In some embodiments, the vessel 4 of the present disclosure is made from an injection molded polymer, for example polystyrene, polycarbonate or any other appropriate polymer as identified by one of skill in the art. In an embodiment, the polymer is optically transparent and non-cytotoxic. Since the materials are made from lightweight polymers and the vessel 4 is pre-sterilized during manufacture, the vessel 4 itself is disposable and there is no need for the end user to sterilize components of the system prior to use.

In some embodiments, the top portion 12 or the bottom portion 16 of the vessel sidewall 10, may have one or more areas that may contain gas permeable/liquid impermeable film or membrane. In embodiments where this gas permeable/liquid impermeable film or membrane is located in an area of the vessel 4 that will contact the cell suspension, improved gas exchange with the external environment is achieved. As such, in some embodiments, the areas are located in the lower half of the sidewall 10 or in the bottom interior surface 70.

In describing the manufacturing and assembly process, the impeller assembly 58, the top portion 12 and the bottom portion 16 of the vessel body 8 are molded separately and treated as discussed. Thereafter, the magnet 94 is placed in the magnet receptacle 62. As previously noted, in another embodiment, the magnet 94 itself is over-molded and therefore integral with the impeller assembly 58. The impeller assembly 58 is placed within a shaft receptacle 42 of the top portion 12. The o-ring 82 is slipped over the top end of the shaft 46 and contacted with the receiving groove 130. The top portion 12 and the bottom portion 16 of the vessel 4 are then permanently affixed to one another by, for example, ultrasonic welding along the weld line 20 thereby creating a completely and permanently integral unit. Similarly, a disc top 122 is welded in position sealing the shaft receptacle 42. In other embodiments, the parts are laser welded or attached by means of adhesives. In embodiments having one or more necked access ports 32 and sealing caps 28, the sealing caps 28 are put into place and the unit is effectively sealed for shipment. The integral unit may then be sterilized. As most cell culture procedures are carried out under aseptic conditions by practicing the so-called sterile technique, the pre-sterilization of the vessel 4 provides the culture chamber to be maintained in a sterile, closed environment. It is advantageous to have the cell culture process carried out in a system where the culture chamber is functionally closed to the external environment, with the sterile integrity maintained from the time the device is manufactured until it has been disposed of. One method of pre-sterilizing includes gamma irradiation. Other sterilization methods known to those skilled in the art including ethylene oxide or electron beam irradiation treatment could also be used.

Based on the manufacturing approach and since the weld line 20 exists in the sidewall 10 region of the vessel 4, the impeller assembly 58 may be sized such that the blades 50, 54 extend nearly the full diameter of the vessel 4. In an embodiment, the impeller blades 50, 54 extend approximately 50-95% of the vessel's radius, as measured from the central axis A-A' to the sidewall 10. In another embodiment, at least one blade 50, 54 extends 75-95% of the vessel's radius but due the design and manufacturing approach, may extend any distance.

To operate the system of the present disclosure, liquid (such as a culture media including cells) is delivered through the one or more access ports 32 of the container. The liquid is added until it reaches a fluid level which is preferably below the top edge of the blades 50, 54 and the top of the baffles 24 but above the lower portion 60 of the major blades 50.

Once the liquid is in the vessel 4, the vessel 4 is placed upon a magnetic stirring device (not shown) and the stirring device causes the magnetic stir bar 94 to spin within the vessel 4. As a result, the impeller assembly 58 including the shaft 46 and the blades 50, 54 is also caused to rotate within the vessel 4. The rotation of the assembly 58 causes the fluid to stir within the container. Alternatively, the impeller 58 may be rotated by a motorized mechanism engaging the top of the shaft 46. The shape of the blades 50, 54 and the interaction with the baffles 24 causes the liquid to circulate from a position near the top of the fluid level to a position near the bottom of the fluid level. The center nub 112 prevents material from accumulating at the center of the bottom interior surface 70. Since the upper portion 52 of the major blades 50 extends above the fluid level, the surface area of the liquid in the container is effectively increased and continually agitated, resulting in aeration of the liquid.

The apparatus is used to stir cells suspended in a culture media. The cells may also be attached to microcarriers suspended in the culture medium. This mixing can be performed over a relatively long time (i.e., from several hours up to several months) but must not produce great stress to cells suspended in the liquid. The mixing must be effective such that the liquid cycles from the bottom of the apparatus to the surface, and back again. Typically, the cells are maintained at about 27° C.-37° C. and mixed at 5 to 300 rpm. Of course, these conditions can be varied depending on the particular cells or application. Cells or cellular materials may be harvested through the access ports by means of pipette, pouring, or pumping.

According to an aspect (1) of the present disclosure, a vessel for culturing cells is provided. The vessel comprises: a vessel body having a top portion, a bottom portion comprising a bottom interior surface, and a cylindrical sidewall; an impeller assembly inside the vessel body comprising a top portion rotatably coupled to the top portion of the vessel body, the impeller assembly having a plurality of planar blades, a central axis, a flexible shaft extending down from the top portion of the impeller assembly, a magnet receptacle molded within the plurality of planar blades, a magnet within the magnet receptacle, and an impeller o-ring coupled to a bottom surface of the planar blades; and a plurality of positioning nubs coupled to the bottom interior surface of the vessel body, spaced from an inside edge of the impeller o-ring.

According to an aspect (2) of the present disclosure, the vessel of aspect (1) is provided, wherein the plurality of positioning nubs is three positioning nubs, each nub spaced circumferentially from each of the other nubs at an approximately equal distance.

According to an aspect (3) of the present disclosure, the vessel of aspect (2) is provided, wherein each of the nubs have a conical shape.

According to an aspect (4) of the present disclosure, the vessel of aspect (2) is provided, wherein each of the nubs have a cylindrical shape.

According to an aspect (5) of the present disclosure, the vessel of any of aspects (1)-(4) is provided, wherein the vessel body comprises a polymeric material.

According to an aspect (6) of the present disclosure, the vessel of any of aspects (1)-(5) is provided, wherein the plurality of planar blades is four planar blades coupled to the flexible shaft, each blade disposed at 90 degrees relative to the blades adjacent to it.

According to an aspect (7) of the present disclosure, the vessel of any of aspects (1)-(6) is provided, further comprising: a plurality of baffles, each baffle integral with the sidewall of the vessel body originating at the bottom interior surface and extending vertically to a predetermined distance up the sidewall.

According to an aspect (8) of the present disclosure, the vessel of aspect (7) is provided, wherein each baffle terminates in an elliptical shape.

According to an aspect (9) of the present disclosure, the vessel of any of aspects (7)-(8) is provided, wherein the plurality of baffles is three baffles, each baffle is spaced an equal distance from each of the other baffles around a perimeter defined by the cylindrical sidewall.

According to an aspect (10) of the present disclosure, the vessel of any of aspects (1)-(9) is provided, wherein the vessel body further comprises a radius measured by the distance from the central axis to the sidewall, and further wherein at least one of the blades extends about 50 to 95% of the radius of the vessel body toward the cylindrical sidewall.

According to an aspect (11) of the present disclosure, the vessel of any of aspects (1)-(10) is provided, wherein each blade comprises a bottom edge spaced from about 0.05 inches to about 0.5 inches from the bottom interior surface.

According to an aspect (12) of the present disclosure, the vessel of any of aspects (1)-(11) is provided, wherein the impeller assembly is sealed inside the vessel body.

According to aspect (13) of the present disclosure, a vessel for culturing cells. The vessel comprises: a vessel body having a top portion, a bottom portion comprising a bottom interior surface, and a cylindrical sidewall; an impeller assembly inside the vessel body comprising a top portion rotatably coupled to the top portion of the vessel body, the impeller assembly having a plurality of planar blades, a central axis, a flexible shaft extending down from the top portion of the impeller assembly, a magnet receptacle molded within the plurality of planar blades, a magnet within the magnet receptacle, and an impeller o-ring coupled to a bottom surface of the planar blades; a plurality of positioning nubs coupled to the bottom interior surface of the vessel body, spaced from an inside edge of the impeller o-ring; and a center nub coupled to the bottom interior surface of the vessel body coincident with the central axis of the impeller assembly.

According to an aspect (14) of the present disclosure, the vessel of aspect (13) is provided, wherein the plurality of baffles is three baffles, each baffle is spaced an equal distance from each of the other baffles around a perimeter defined by the cylindrical sidewall.

According to an aspect (15) of the present disclosure, the vessel of any of aspects (13)-(14) is provided, wherein the vessel body further comprises a radius measured by the distance from the central axis to the sidewall, and further wherein at least one of the blades extends about 50 to 95% of the radius of the vessel body toward the cylindrical sidewall.

According to an aspect (16) of the present disclosure, the vessel of any of aspects (13)-(15) is provided, wherein the plurality of positioning nubs is three positioning nubs, each nub spaced circumferentially from each of the other nubs at an approximately equal distance.

According to an aspect (17) of the present disclosure, the vessel of aspect (16) is provided, wherein each of the nubs have a conical shape.

According to an aspect (18) of the present disclosure, the vessel of any of aspects (13)-(16) is provided, wherein the center nub has a cylindrical shape or a conical shape.

According to an aspect (19) of the present disclosure, the vessel of any of aspects (13)-(18) is provided, wherein the vessel body is a polymeric material.

According to an aspect (20) of the present disclosure, the vessel of any of aspects (13)-(19) is provided, wherein the plurality of planar blades is four planar blades coupled to the flexible shaft, each blade disposed at 90 degrees relative to the blades adjacent to it.

EXAMPLES

Embodiments of the present disclosure are further described below with respect to certain exemplary and specific embodiments thereof, which are illustrative only and are not intended to be limiting. The following Examples demonstrate the utility and effectiveness of using a plurality of positioning nubs 98 to minimize the perpendicular or lateral movement of the impeller assembly 58 to prevent causing damage to cells and microcarriers in a vessel for culturing cells.

Materials

The Cytodex-1 microcarriers (GE Healthcare #17-0448-01) and enhanced attachment microcarriers (Corning #3779) were used according to the manufacturer's recommendations. Vero cells (ATCC #CCL81™) were cultured in DMEM (Corning #10-010) supplemented with 2 mL L-glutamine (Corning #25-005), 1×MEM NEAA (Corning #25-025) and 10% fetal bovine serum (Corning #35-010). The commercially available 1 L disposable spinner flasks (Corning #3580) and 1 L glass spinner flasks (Corning #4500-1L) were supplied by Corning Incorporated.

Methods and Procedures

Microcarriers were added to spinner flasks at 10 cm$^2$/mL in reduced-serum culture medium 0.5% serum). The flasks were equilibrated in a 5% CO$_2$ incubator at 37° C. for 1 to 2 hours for media equilibration. Vero cells were seeded at a density of 15,000 cells/cm$^2$ and the culture was mixed continuously at 30 rpm during cell attachment. After the cells were attached to the microcarriers the media was adjusted to 5% serum. The culture was expanded for 5 days with a media exchange on day 3. Cells and microcarriers were visualized using a Zeiss Axiovert 40 C inverted light microscope at 5× and 10× magnification. Cells were quantified daily using a Nucleocounter NC-200 automated cell counter.

Comparative Example 1

Figure 12B:
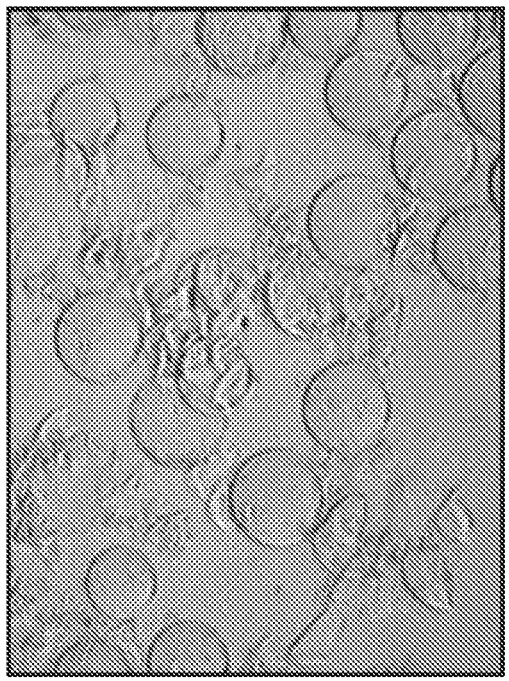
FIG. 12B is an image showing Cytodex-1 microcarriers cultured in a commercially available 1 L disposable spinner flask.
Figure 12A:
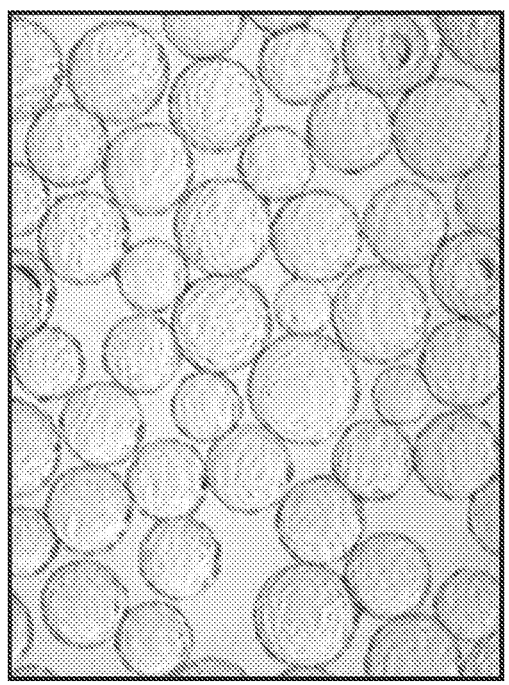
FIG. 12A is an image showing Cytodex-1 microcarriers cultured in a non-disposable 1 L glass spinner flask.

Traditional Glass Spinner Flask Vessel and Disposable Spinner Flask Vessel with Microcarriers The images shown in FIGS. 12A and 12B were both captured on Day 3 of the culture at 10× magnification. The FIG. 12A image shows Cytodex-1 microcarriers in a non-disposable 1 L glass spinner flask and the FIG. 12B image shows the Cytodex-1 microcarriers in a commercially available 1 L disposable spinner flask. FIG. 12A demonstrates that Cytodex-1 microcarriers can be successfully cultured in non-disposable 1 L glass spinner flasks with no observable damage to the cells or microcarriers. The non-disposable 1 L glass spinner flasks has a rigid impeller assembly that is secured to the top surface and is spaced from the bottom surface of the flask so that no contact is made between the impeller assembly and any additional surface of the flask. FIG. 12B demonstrates that the Cytodex-1 microcarriers are significantly damaged in the commercially available 1 L disposable spinner flask. The images highlight that the commercially available 1 L disposable spinner flask is incompatible with Cytodex 1 microcarriers.

Comparative Example 2

Figure 13B:
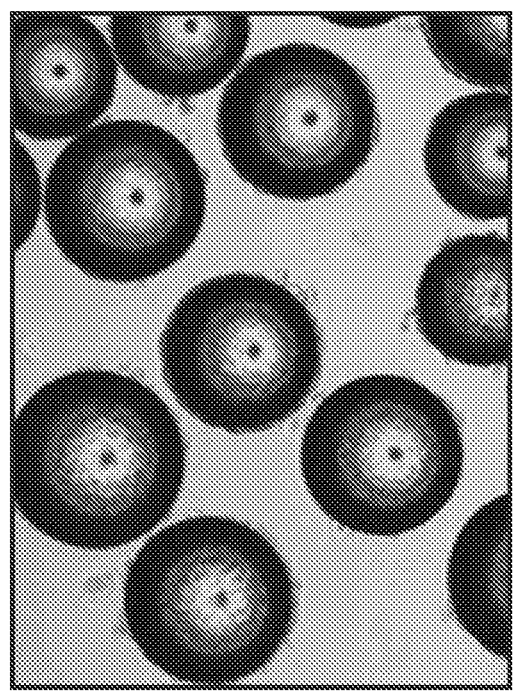
FIG. 13B is an image showing enhanced attachment microcarriers with Vero cells cultured in a commercially available 1 L disposable spinner flask according to an embodiment.
Figure 13A:
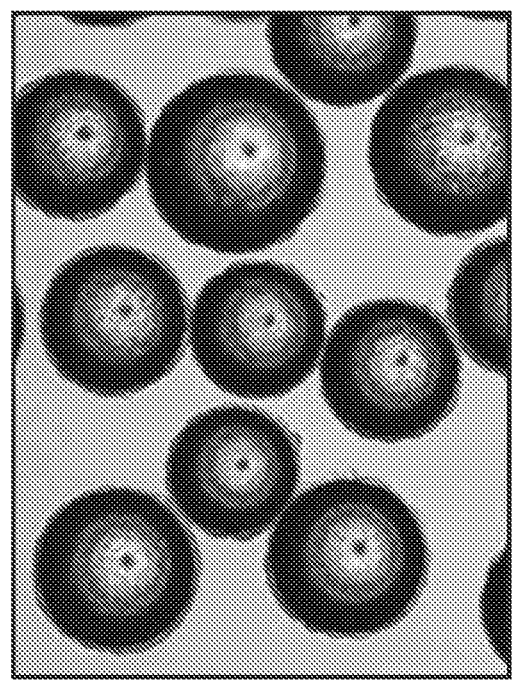
FIG. 13A is an image showing enhanced attachment microcarriers with Vero cells cultured in a non-disposable 1 L glass spinner flask.

Traditional Glass Spinner Flask Vessel and Disposable Spinner Flask Vessel With Microcarriers Having Cells The images shown in FIGS. 13A and 13B were both captured on Day 3 of the culture at 10× magnification. The image in FIG. 13A displays several enhanced attachment microcarriers with a layer of Vero cells still layered on the surface in a non-disposable 1 L glass spinner flask. FIG. 13A demonstrates that the non-disposable 1 L glass spinner flask promotes cell growth to the microcarriers since a healthy, confluent monolayer of cells can be observed. The image in FIG. 13B also displays several enhanced attachment microcarriers but here the layer of Vero cells are sheared from the surface from using the commercially available 1 L disposable spinner flask. FIG. 13B demonstrates the damage caused to the Vero cells in the commercially available 1 L disposable spinner flask since it can be observed in FIG. 13B that the microcarriers have a majority of the cells removed from the surface as well as microcarriers with cells that are peeling off. The inherent wobble and contact of the impeller assembly of the commercially available 1 L disposable spinner flask create the physical damage to the cells and microcarriers.

Prophetic Example 1

Disposable Spinner Flask With Positioning Nubs

Figure 14B:
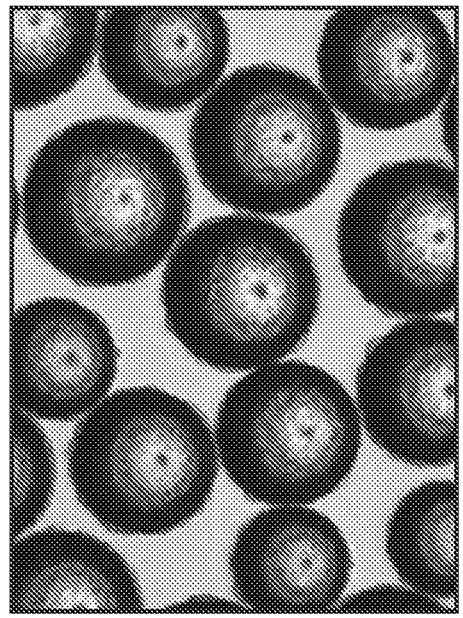
FIG. 14B is a prophetic image showing enhanced attachment microcarriers with Vero cells cultured in an embodiment of a 1 L disposable spinner flask with a plurality of positioning nubs.
Figure 14A:
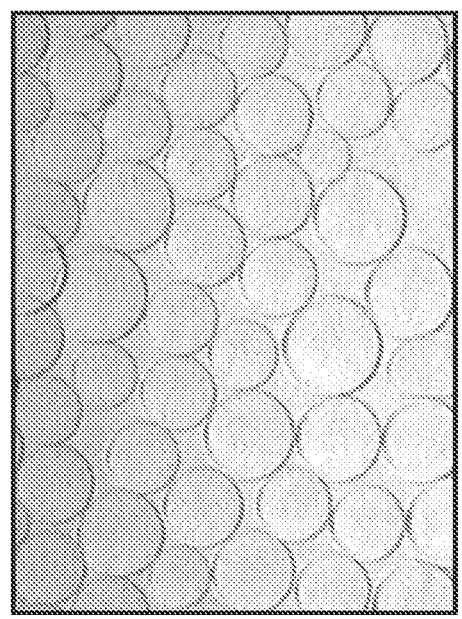
FIG. 14A is a prophetic image showing Cytodex-1 microcarriers cultured in an embodiment of a 1 L disposable spinner flask with a plurality of positioning nubs.

This prophetic example modifies a commercially available 1 L disposable spinner flask by adding a plurality of positioning nubs spaced from an inside edge of an impeller o-ring on an impeller assembly. As described in the embodiments of the Detailed Description above, utilizing a center nub positioned on the bottom of the vessel combined with a plurality of positioning nubs spaced from an inside edge of an impeller o-ring would prevent the perpendicular or lateral movement of the impeller thereby preventing the impeller wobble. Eliminating this unwanted impeller assembly movement will mimic the conditions of the non-disposable 1 L glass spinner flask and minimize the damage done to microcarriers and microcarriers having cells shown in FIGS. 12A and 13A. The prophetic image shown in FIG. 14A would be captured on Day 3 of the culture at 5× magnification and would be expected to display Cytodex 1 microcarriers in a 1 L disposable spinner flask with a plurality of positioning nubs. The prophetic image shown in FIG. 14B would be captured on Day 3 of the culture at 10× magnification and would be expected to display Vero cells cultured on enhanced attachment microcarriers in a 1 L disposable spinner flask with a plurality of positioning nubs. Both FIGS. 14A and 14B would be expected to show that Cytodex 1 microcarrier and Vero cell damage is visibly reduced or eliminated when impeller wobble is prevented by the center nub positioned on the bottom of the vessel and the plurality of positioning nubs spaced from an inside edge of an impeller o-ring.

It is not intended that the scope of the present disclosure is to be limited by the Examples described and illustrated above, but instead it is intended the scope of the present disclosure will be determined by the appended claims and their equivalents.

It is also to be understood that variations and modifications can be made on the aforementioned structures and methods without departing from the concepts of the present disclosure, and further it is to be understood that such concepts are intended to be covered by the following claims unless these claims by their language expressly state otherwise.

What is claimed is:

1. A vessel for culturing cells, comprising:
a vessel body having a top portion, a bottom portion comprising a bottom interior surface, and a cylindrical sidewall;
an impeller assembly inside the vessel body comprising a top portion rotatably coupled to the top portion of the vessel body, the impeller assembly having a plurality of planar blades, a central axis, a flexible shaft extending down from the top portion of the impeller assembly, a magnet receptacle molded within the plurality of planar blades, a magnet within the magnet receptacle, and an impeller o-ring, where each of the plurality of planar blades comprises a bottom surface and the impeller o-ring is coupled to each of the bottom surfaces of the planar blades; and
a plurality of positioning nubs coupled to the bottom interior surface of the vessel body, spaced from an inside edge of the impeller o-ring.

2. The vessel of claim 1, wherein the plurality of positioning nubs is three positioning nubs, each nub spaced circumferentially from each of the other nubs at an approximately equal distance.

3. The vessel of claim 2, wherein each of the nubs have a conical shape.

4. The vessel of claim 2, wherein each of the nubs have a cylindrical shape.

5. The vessel of claim 1, wherein the vessel body comprises a polymeric material.

6. The vessel of claim 1, wherein the plurality of planar blades is four planar blades coupled to the flexible shaft, each blade disposed at 90 degrees relative to the blades adjacent to it.

7. The vessel of claim 1, further comprising:
a plurality of baffles, each baffle integral with the sidewall of the vessel body originating at the bottom interior surface and extending vertically to a predetermined distance up the sidewall.

8. The vessel of claim 7, wherein each baffle terminates in an elliptical shape.

9. The vessel of claim 7, wherein the plurality of baffles is three baffles, each baffle is spaced an equal distance from each of the other baffles around a perimeter defined by the cylindrical sidewall.

10. The vessel of claim 1, wherein the vessel body further comprises a radius measured by the distance from the central axis to the sidewall, and further wherein at least one of the blades extends about 50 to 95% of the radius of the vessel body toward the cylindrical sidewall.

11. The vessel of claim 1, wherein each blade comprises a bottom edge spaced from about 0.05 inches to about 0.5 inches from the bottom interior surface.

12. The vessel of claim 1, wherein the impeller assembly is sealed inside the vessel body.

13. A vessel for culturing cells, comprising:
a vessel body having a top portion, a bottom portion comprising a bottom interior surface, and a cylindrical sidewall;
an impeller assembly inside the vessel body comprising a top portion rotatably coupled to the top portion of the vessel body, the impeller assembly having a plurality of planar blades, a central axis, a flexible shaft extending down from the top portion of the impeller assembly, a magnet receptacle molded within the plurality of planar blades, a magnet within the magnet receptacle, and an impeller o-ring, where each of the plurality of planar blades comprises a bottom surface and the impeller o-ring is coupled to each of the bottom surfaces of the planar blades; and;
a plurality of positioning nubs coupled to the bottom interior surface of the vessel body, spaced from an inside edge of the impeller o-ring; and
a center nub coupled to the bottom interior surface of the vessel body coincident with the central axis of the impeller assembly.

14. The vessel of claim 13, further comprising a plurality of baffles, each baffle integral with the sidewall of the vessel body,
wherein each baffle is spaced an equal distance from each of the other baffles around a perimeter defined by the cylindrical sidewall.

15. The vessel of claim 13, wherein the vessel body further comprises a radius measured by the distance from the central axis to the sidewall, and further wherein at least one of the blades extends about 50 to 95% of the radius of the vessel body toward the cylindrical sidewall.

16. The vessel of claim 13, wherein the plurality of positioning nubs is three positioning nubs, each nub spaced circumferentially from each of the other nubs at an approximately equal distance.

17. The vessel of claim 16, wherein each of the nubs have a conical shape.

18. The vessel of claim 13, wherein the center nub has a cylindrical shape or a conical shape.

19. The vessel of claim 13, wherein the vessel body is a polymeric material.

20. The vessel of claim 13, wherein the plurality of planar blades is four planar blades coupled to the flexible shaft, each blade disposed at 90 degrees relative to the blades adjacent to it.

* * * * *